United States Patent [19]

Sperling

[11] Patent Number: 5,071,624
[45] Date of Patent: Dec. 10, 1991

[54] SYSTEM FOR INTRODUCING A SAMPLE SUBSTANCE INTO A SPECTROSCOPICAL ANALYTICAL INSTRUMENT

[75] Inventor: Michael Sperling, Sipplingen, Fed. Rep. of Germany

[73] Assignee: Bodenseewerk Perkin Elmer GmbH, Uberlingen, Fed. Rep. of Germany

[21] Appl. No.: 531,171

[22] Filed: May 31, 1990

[30] Foreign Application Priority Data

Jun. 1, 1989 [DE] Fed. Rep. of Germany ....... 3917840

[51] Int. Cl.$^5$ .................... G01N 30/00; G01N 21/00; G01N 35/00
[52] U.S. Cl. ...................... 422/69; 422/63; 422/82; 422/103; 73/863.72; 73/863.73; 73/864.83; 436/161; 210/198.2
[58] Field of Search ............. 422/63, 69, 70, 81, 422/82, 103; 73/863.72, 863.73, 864.83; 251/61 62; 436/161; 210/198.2, 659; 137/566, 567, 597

[56] References Cited

U.S. PATENT DOCUMENTS

| | | | |
|---|---|---|---|
| 3,990,853 | 11/1976 | Godin | 422/82 |
| 4,302,421 | 11/1981 | Baker | 422/64 |
| 4,315,754 | 2/1982 | Ruzicka | 422/81 |
| 4,726,932 | 2/1988 | Feier et al. | 73/863.72 |
| 4,837,157 | 6/1989 | Turnell et al. | 422/70 |
| 4,843,016 | 6/1989 | Fine | 422/70 |
| 4,872,992 | 10/1989 | Oquendo et al. | 210/198.2 |

FOREIGN PATENT DOCUMENTS 0681196 5/1966 Belgium .

OTHER PUBLICATIONS

Fang et al., "Fundamental and Practical Considerations in the Design of On-Line Column Preconcentration for Flow-Injection Atomic Spectrometric Systems", Analytica Chimica Acta, 200 (1987) pp. 35-49.
Hartenstein et al., "Sensitivity Enhancement for Flow Injection Analysis-Inductivelty Coupled Plasma Atomic Emission Spectrometry Using an On-Line Preconcentrating Ion-Exchange Column", 1985, pp. 21-25.

Primary Examiner—Robert J. Warden
Assistant Examiner—Theresa A. Trembley
Attorney, Agent, or Firm—Thomas P. Murphy; Edwin T. Grimes

[57] ABSTRACT

A system for introducing a sample substance into a spectroscopical analytical instrument which includes a first pump which, when on, pumps a sample liquid and a buffer liquid, and a second pump which, when on, pumps an eluting liquid and rinsing liquid. The system includes an ion exchanger column for retaining the elements of the sample to be determined and which can be eluted by the eluting liquid. A dosing capillary serves to introduce the sample into the furnace of an atomic absorption spectrometer. A valve has a first position wherein the first end of the ion exchanger column communicates with the first pump and the second end communicates with a waste outlet port, and the dosing capillary communicates with a source of displacing fluid; and a second position wherein the second end of the ion exchanger column communicates with the second pump and the first end communicates with the dosing capillary.

10 Claims, 4 Drawing Figures

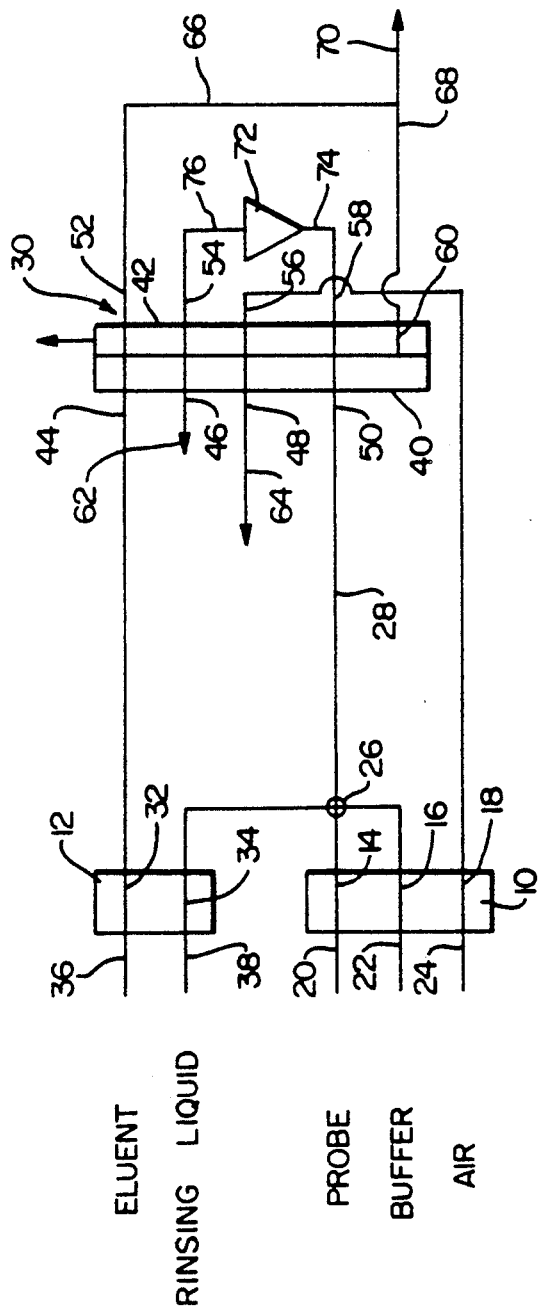
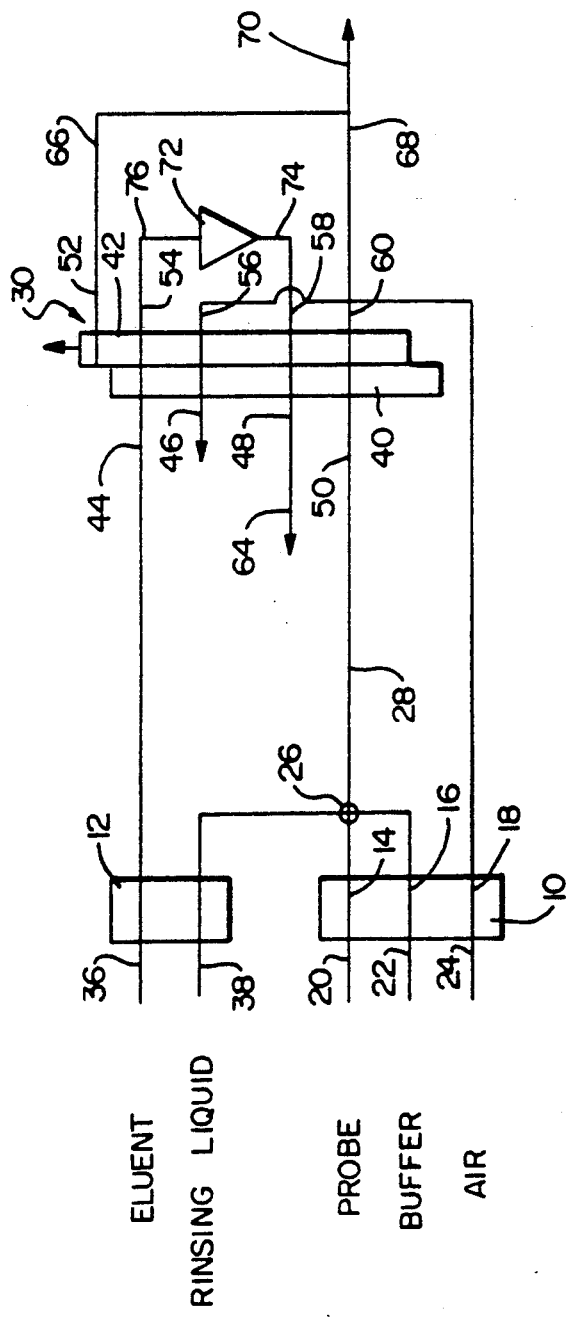

SYSTEM FOR INTRODUCING A SAMPLE SUBSTANCE INTO A SPECTROSCOPICAL ANALYTICAL INSTRUMENT

FIELD OF INVENTION

The invention relates to analytical instruments and, more particularly, to a system for introducing a sample substance into a spectroscopical analytical instrument.

BACKGROUND OF THE INVENTION

An arrangement for accumulating sample substances for spectroscopical purposes by a flow injection technique is known from a publication by Olsen et al in the journal, "The Analyst", vol. 108, 905–917. Water, a buffer liquid in the form of ammonium acetate, and an eluting liquid in the form of nitric acid are pumped into parallel hose conduits by a peristaltic pump. An injection valve is provided in the hose conduit into which the water is pumped. The injection valve has a passage and a sample loop, which is arranged to be optionally connected to the flow in the hose conduit. When the passage is connected to the hose conduit, a flow of sample liquid is passed through the sample loop so that the sample loop is filled with sample liquid. After switching over the injection valve, the sample loop filled with sample liquid is connected to the hose conduit conducting the water flow so that the sample liquid is carried along by the flow of water. Either the water or the sample liquid is mixed with the buffer liquid and flows through the ion exchanger when a valve arrangement is in its first valve position, namely from the first end of the ion exchanger column to the second end thereof. The second end communicates with a waste outlet port. In the first valve position of the valve arrangement, the eluting liquid flows to a nebulizer and is sprayed into the flame of an atomic absorption spectrometer. An accumulation of the sample in the ion exchanger column follows. Subsequently, the valve arrangement is switched over to a second valve position. In this second valve position, the water—and the ammonium acetate hose conduits —communicate with the waste outlet port. The second end of the ion exchanger column communicates with the hose conduit conducting the eluting liquid. The first end of the ion exchanger column communicates with the nebulizer of the atomic absorption spectrometer. The eluting liquid flows through the ion exchanger column in the reverse direction compared to the previous flow direction and elutes the accumulated elements of the sample which are to be determined into the nebulizer and thus into the burner of the atomic absorption spectrometer.

By virtue of a publication by Hartenstein et al in by Zhaolun Fang et al in "Analytica Chimica Acta" 200 (1987), 35–49, an arrangement is known in which a first sample liquid with an associated buffer liquid, and a second sample liquid with an associated buffer liquid, are each pumped by a first peristaltic pump. The sample liquids are mixed with the associated buffer liquids in conduit coils which are connected downstream to the peristaltic pump. The mixture of sample liquid and buffer liquid obtained in this way is passed to a first valve. In a first valve position of the first valve, the sample and buffer liquids are passed to a first end of an associated ion exchanger column. Each of the second ends of the ion exchanger columns communicate with a waste outlet port. Then, the two ion exchanger columns are parallelly charged with sample liquid, the sample being accumulated within the column. A second peristaltic pump pumps an eluting liquid and water. In the first position of the valve, the water is passed to the nebulizer of a plasma burner. In this first position of the valve, the eluting liquid communicates with a waste outlet port. In the second position of the valve, the eluting liquid passes to the second end of an ion exchanger column, the first end of which then communicates with the nebulizer. The ion exchanger column to which the eluting liquid is supplied is selected by a changeover valve.

By the use of two ion exchanger columns which are parallelly charged, the analyzing period of time can be approximately halved. During the charging of the ion exchanger column, water instead of the eluting liquid is passed to the nebulizer. The water rinses the nebulizer and stabilizes the plasma.

In the prior art method, the eluting liquid is passed with the eluted, accumulated sample to a nebulizer which sprays the liquid into the flame of an atomic absorption spectrometer.

It is also known to use a flow injection method in atomic absorption spectroscopy by inserting a sample, which is pretreated, into a furnace for thermoelectric atomization ("ANALYST" vol. 109 (March 1984), 323–325). However, the pretreated sample from the flow injection system is first passed into an open sample vessel and is dosed from this sample vessel into the furnace of the atomic absorption spectrometer. Thus, the substantial advantages of the flow injection technique, such as the entire occlusion of the sample from the environment and the possibility of treating very small sample amounts, are lost.

In a publication by Hamann, Meier, and Kettrup in "Fresenius Zeitschrift fur analytische Chemie", 1989, vol. 334, pages 231 to 234, there is described the determination of phenoxycarboxylic acid herbicides using high pressure liquid chromatographies. Therein, the herbicides are enriched in a precolumn.

A publication by Jackson and Haddad in the "Journal of Chromatography", vol. 439 (1988), pages 37 to 48, describes a flow injection arrangement including anion preconcentration, wherein the preconcentrated sample is passed through a UV absorption detector.

German Patent No. 2,900,066, corresponding to U.S. Pat. No. 4,294,126, describes a sample feeder in which the samples are arranged in sample receptacles at a turntable. A take up tube takes up sample liquid from the sample receptacles by suction and delivers the same through a sample infeed opening into a furnace for electro-thermally atomizing the sample. A measuring light beam of an atomic absorption spectrometer is passed through the furnace.

SUMMARY OF THE INVENTION

It is an object of the invention to increase the detection limits in atomic absorption spectroscopy and, at the same time, obtain a high degree of automation of the analysis.

According to the invention, this and other objects are achieved by the provision of a new and improved system for introducing a sample substance into a spectroscopical analytical instrument, which includes first pumping means for pumping a sample liquid and a buffer liquid and second pumping means for pumping an eluting liquid. An ion exchanger column serves to retain elements of the sample which are to be determined and for eluting said elements by the eluting liquid. Means are provided for introducing the sample into the spectroscopical analytical instrument. A valve is provided which is movable between a first valve position wherein one end of the ion exchanger is connected to the first pumping means and the second end is connected to a waste outlet port, and the means for introducing the sample into the analytical instrument is connected to a source of displacing fluid, and a second valve position wherein the other end of the ion exchanger column is connected to the second pumping means and the first end is connected to the means for introducing sample into the analytical instrument. The means for introducing sample into the analytical instrument include a dosing capillary having a first end connected to the valve means and a second end insertable into a port in the analytical instrument. Thus, an accumulation of the looked for element is effected in the ion exchanger column. Unwanted components of the sample are not retained in the ion exchanger column and, thereby, are eliminated from the atomic absorption measurement. This is accomplished in a flow injection system, which is closed to the environment. However, the sample components retained in the ion exchanger column are not eluted into the nebulizer of a burner, such as in the prior art arrangements, and also are not passed into an open sample vessel, but go directly into a dosing capillary which can be introduced into the furnace of an atomic absorption spectrometer. It has been found that the looked for components retained in the ion exchanger column can be eluted with an amount of eluting liquid accommodated by the dosing capillary, the volume of the dosing capillary being not larger than the accommodation capacity of the furnace for the sample liquid. While a sample is passed through the ion exchanger column to accumulate the looked for components of the sample therein, the dosing capillary is simultaneously introduced into a sample inlet port of the furnace, and the eluting agent accommodated therein is forced into the furnace by a displacing fluid.

In a preferred embodiment of the invention, the first pumping means are switched on during a first operation period and are switched off during a consecutive second operation period. The second pumping means are switched off during the first operation period and are switched on during the second operation period. Part way through the second operation period, the valve means is switched over from the first valve position to the second valve position. The displacing fluid is pumped by the first pumping means. This displacing fluid is advantageously a gas, such as air, for example.

In the second operation period, the second pumping means pumps the rinsing liquid into a collecting conduit. During the first operation period, the first pumping means pumps sample and buffer solution through said collecting conduit to the valve means, which communicates in the second valve position with an outlet port. That is, a sample port and a buffer solution port are joined at the outlet side of the first pumping means to form a collecting conduit, which communicates with the collecting conduit port of the valve means. A rinsing liquid port communicates through the second pumping means and a connecting conduit with the collecting conduit. The collecting conduit port communicates in a first valve position with the first end of the ion exchanger column and in the second valve position with an outlet port.

In a preferred embodiment, the analytical instrument is an atomic absorption spectrometer with a furnace for electrothermal atomization of the sample. The dosing capillary for supplying the sample can be introduced into a sample inlet opening in the furnace. The capacity of the dosing capillary is not larger than the accommodation capacity of the furnace.

It is advantageous to have the ion exchanger column taper from its second end to its first end. Preferably, the first and the second pumping means are peristaltic pumps, respectively.

There has thus been outlined rather broadly the more important features of the invention in order that the detailed description thereof that follows may be better understood, and in order that the present contribution to the art may be better appreciated. There are, of course, additional feature of the invention that will be described more fully hereinafter. Those skilled in the art will appreciate that the conception on which this disclosure is based may readily be utilized as the basis of the designing of other assemblies and systems for carrying out the various purposes of the invention. It is important, therefore, that this disclosure be regarded as including such equivalent assembles and routines as do not depart from the spirit and scope of the invention.

One embodiment of the invention has been chosen for purposes of illustration and description, and is shown in the accompanying drawings forming a part of the specification.

BRIEF DESCRIPTION OF THE DRAWINGS

The drawings, not drawn to scale, include:

FIG. 1, which is a schematic illustration of a system for accumulating sample substance for an atomic absorption spectrometer in a first valve position, the accumulation being made in a flow injection system and the atomization being made thermoelectrically in a furnace;

FIG. 2, which shows the same arrangement in a second valve position;

DETAILED DESCRIPTION OF A PRESENTLY PREFERRED EMBODIMENT OF THE INVENTION

Figure 3:
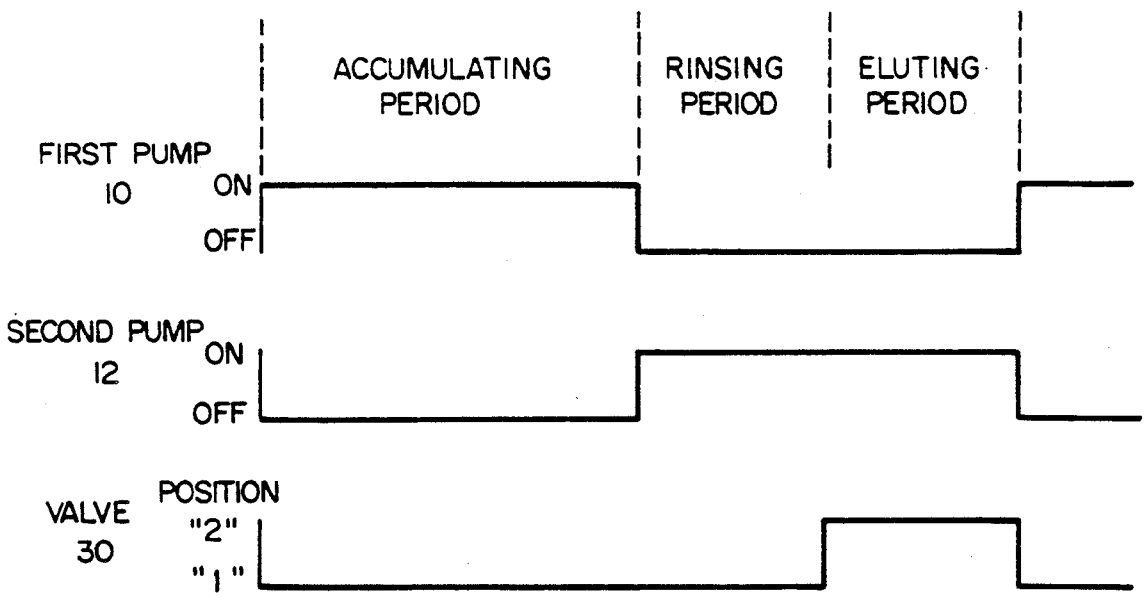
FIG. 3, which illustrates the conditions of the elements of the system of FIGS. 1 and 2 in the course of an analyzing cycle.

In FIGS. 1 and 2, the numeral 10 designates first pumping means in the form of a peristaltic pump, and numeral 12 designates second pumping means also in the form of a peristaltic pump.

The peristaltic pump of the first pumping means 10 comprises three hose conduits 14, 16, and 18. The hose conduit 14 is connected to a sample inlet port 20, which can be connected to a dosing tube, for example, which aspirates sample from a sample vessel on a turntable or which aspirates a blind solution or a calibration solution. The hose conduit 16 is
d to a buffer inlet port 22 through which a buffer solution can be aspirated. The hose conduit 18 is connected to an inlet port 24, through which a displacing fluid is aspirated. In the preferred embodiment, the displacing fluid is simply air. The hose conduits 14 and 16 of the pumping means 10 are joined at a junction point 26. A collecting conduit 28 originating from the junction point 26 leads to the valve means 30.

The peristaltic pump of the second pumping means 12 comprises two hose conduits 32 and 34. The hose conduit 32 is connected to a port 36 through which an eluting liquid (eluent) can be aspirated, such as hydrochloric acid, for example. The hose conduit 34 is connected to an inlet port 38. Through the inlet port, a rinsing liquid such as deionized water, for example, can be aspirated. The hose conduit 34 is also connected at the junction point 26 to the collecting conduit 28.

In the embodiment described, the valve means are illustrated as a sliding valve. The valve means comprise a stationary valve member 40 and a valve member 42 which is movable between a first valve position (FIG. 1) and a second valve position (FIG. 2). The stationary valve member 40 has a first port 44, a second port 46, a third port 48, and a fourth port 50. The movable valve member has a fifth port 52, a sixth port 54, a seventh port 56, an eighth port 58, and a ninth port 60. In the first valve position (FIG. 1), the first port 44 communicates with the fifth port 52. The second port 46 communicates with the sixth port 54. The third port 48 communicates with the seventh port 56. The fourth port 50 communicates with the eighth port 58. In the second valve position (FIG. 2), the first port 44 communicates with the sixth port 54. The second port 46 communicates with the seventh port 56. The third port 48 communicates with the eighth port 58. The fourth port 50 communicates with the ninth port 60.

The hose conduit 32 of the second pumping means 12 is connected to the first port 44 of the valve means 30. The second port 46 communicates with an outlet port 62. A dosing capillary 64 is connected to the third port. The fourth port 50 of the valve means 30 communicates with the collecting conduit 28.

The fifth port 52 and the ninth port 60 communicate through conduits 66 and 68 with an outlet port 70. An ion exchanger column 72 is provided between the sixth port 54 and the eighth port 58. The ion exchanger column 72 has a first end 74 which is connected to the eighth port 58 and a second end 76 which is connected to the sixth port 54 of the valve means 30. The ion exchanger column 72 tapers from the second end 76 to the first end 74. Finally, the seventh port 56 of the valve means 30 communicates with the hose conduit 18 of the first pumping means 10.

Figure 4:
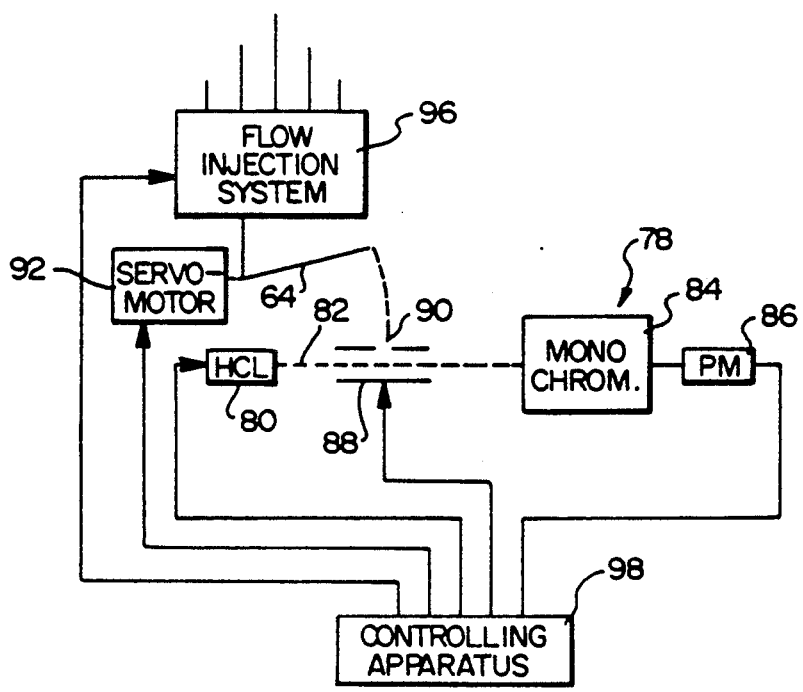
FIG. 4, which is a schematic illustration of an atomic absorption spectrometer with a flow injection system and a furnace for the electro-thermal atomization.

FIG. 4 schematically illustrates an atomic absorption spectrometer 78. The atomic absorption spectrometer 78 has a hollow cathode lamp 80 from which a measuring light beam originates. The light beam passes through a monochromator 84 and impinges upon a detector 86. For atomizing the sample, a furnace 88 is provided which can be heated to atomizing temperature by passing electric current therethrough. The measuring light beam 82 passes through the longitudinal bore of the tubular furnace 88 The furnace 88 has a sample inlet opening 90.

The dosing capillary 64 is introduced by a servo-motor 92 into the sample inlet opening or port in the furnace 88, as indicated by the arc 94 illustrated as a broken line. The flow injection system as a whole, illustrated in FIGS. 1 and 2, is illustrated in FIG. 4 by a block 96. The entire arrangement is controllable by a controlling apparatus 98 for executing a certain program.

FIG. 3 shows the modes of the pumping means 10 and 12 and the valve means 30 in the different periods of operation. In a first operating period, the pumping means 10 is switched on and the pumping means 12 is switched off. The valve means 30 is in the valve position "1". This is the "accumulating" mode, which is illustrated in FIG. 1. In the second operating period, the pumping means 10 is switched off and the pumping means 12 is switched on. During the first half of this operating period, the valve means 30 is still in the valve position "1". Then the "rinsing" function is effected. In the course of the second operating phase, the valve means 30 is switched over to the position "2", resulting in the mode which is illustrated in FIG. 2. This is the "eluting" function. The different conditions are controlled by the controlling apparatus 98 and are suitably synchronized with the function of the atomic absorption spectrometer 78, the furnace 88, and the servo-motor 92.

The mode of operation of the described system is as follows:

In the mode illustrated in FIG. 1, the valve means 30 is in a first valve position. The first pumping means 10 operates while the second pumping means 12 is inoperative. The sample thereby is aspirated through the entrance 20 and the hose conduit 14, and the buffer solution is aspirated through the inlet port 22 and the hose conduit 16. The sample and the buffer solution meet at the junction point 26 and are passed through the collecting conduit 28 to the fourth port of the valve means 30. In the first valve position, the mixture of sample and buffer obtained in this way is passed through the port 58 of the valve means to the first end 74 of the ion exchanger column 72. The mixture flows through the ion exchanger column 72 and through its second end 76 and the ports 54 and 46 of the valve means 30 to the outlet port 62. When the mixture flows through the ion exchanger column 72, the looked for components of the sample are retained in the ion exchanger column 72 and are accumulated. Disturbing or unwanted components (matrix) preponderantly flow through the ion exchanger column 72 and through the outlet port. Thereby, accumulation of the looked for element is achieved. On the other hand, unwanted components are eliminated. These unwanted components can no longer disturb the subsequent measurements in the atomic absorption spectrometer. The amount of the substance which is to be atomized compared to the amount of the looked for component is also considerably reduced. The object of the buffer solution is to generate such a composition of the mixture, e.g., such a pH-value, that the looked for components are actually retained in the ion exchanger column 72. The conically tapering shape of the ion exchanger column 72 causes the looked for components of the sample to be first of all retained in the tip of the ion exchanger column 72. There, the looked for elements are concentrated in a small area and, therefore, can subsequently be eluted very quickly and in a very tight package, as will be explained more fully hereinafter. While accumulation of the looked for components from a sample is accomplished in the described manner, the looked for components of a preceding sample, which were eluted into the dosing capillary 64, are simultaneously supplied to the furnace 88. The dosing capillary 64 is introduced with its free end through the sample inlet opening 90 into the furnace 88. The air aspirated through the inlet port 24 and supplied to the hose conduit 18 by the first pumping means is forced through the port 56 and the port 48 of the valve means into the rear end of the dosing capillary 64 and displaces the eluted sample components contained therein. These components are forced into the furnace 88. Then the dosing capillary is moved out of the furnace 88. The furnace is heated to the atomizing temperature.

Subsequently, the first pumping means 10 are stopped and the second pumping means 12 are switched on. The valve means 30 remains in its first position, FIG. 1. Now, a rinsing liquid is passed from the inlet port 38 through the hose conduit 34, the junction point 26, the collecting conduit 28, the port 50, and the port 58, through the ion exchanger column 72 from its first end 74 to its second end 76 and through the port 54 and the port 46 to the outlet port 62. Thereby, the system is cleaned and the sample residue is removed. The components of the sample retained in the ion exchanger column 72 are not influenced by this rinsing procedure, as is indicated in FIG. 3 by the function "rinsing". The eluting liquid at the inlet port 36 is passed to the outlet port 70.

Then, as the next step, the valve means 30 is switched over to its second valve position. The second pumping means 12 operates while the first pumping means 10 stops. This is illustrated in FIG. 2. In FIG. 3, this corresponds to the function "eluting". Now, eluting liquid such as hydrochloric acid, for example, is passed from the inlet port 36 through the hose conduit 32, the first port 44, and the sixth port 54, through the ion exchanger column 72 from its second end 76 to its first end 74. Thereby, the looked for components of the sample retained in the ion exchanger column 72 are eluted and are conveyed with the eluting liquid into the dosing capillary 64. This can be accomplished with an amount of eluting liquid, which can be entirely accommodated by the dosing capillary 64. The volume of the dosing capillary 64, in turn, is not larger than the accommodation capacity of the furnace 88 for sample liquids.

During the accumulation of the next sample in the way described above, the eluted components are dosed with the eluting liquid from the dosing capillary 64 into the furnace 88.

In the second valve position, the rinsing liquid from the inlet port 38 flows from the hose conduit 38 through the collecting conduit 28 and the ports 50 and 60 of the valve means 30 to the outlet port 70. The collecting conduit is further rinsed.

Although a certain particular embodiment of the invention is herein disclosed for purposes of explanation, further modification thereof, after study of this specification, will be apparent to those skilled in the art to which the invention pertains. Reference should accordingly be had to the appended claims in determining the scope of the invention:

What is claimed is:

1. A system for introducing a sample substance into a spectroscopical analytical instrument comprising, in combination:
   (a) a first pumping means which is on during a first operating phase (10) for pumping a sample liquid and a buffer liquid and off during a second operating phase,
   (b) second pumping means which is on during the second operating phase (12) for pumping an eluting liquid,
   (c) an ion exchanger column (72) for retaining said sample which is to be determined and for eluting said sample by the eluting liquid, said column having a first end (74) and a second end (76),
   (d) means (64) for introducing the sample into the spectroscopical analytical instrument (78), and
   (e) valve means (30) movable between a first valve position wherein the first end (74) of the ion exchanger column (72) is connected via a conduit to the first pumping means (10) and the second end (76) of the ion exchanger column (72) is connected via a conduit to a waste outlet port (62), and the means (64) for introducing the sample into the analytical instrument (78) is connected via a conduit to a source (24) of displacing fluid, and a second valve position wherein the second end (76) of the ion exchanger column (72) is connected via a conduit to the second pumping means (12) and the first end (74) is connected via a conduit to the means (64) for introducing sample into the spectroscopical analytical instrument (78), said valve means being moved to said second valve position while said second pumping means is on, wherein said means for introducing sample into the analytical instrument including a dosing capillary (64) having a first end connected to the valve means (30) and a second end insertable into a port (88) in said analytical instrument (78).

2. A system according to claim 1, wherein said displacing fluid which is in fluid communication with said first pumping means is pumped by the first pumping means (10).

3. A system according to claim 2, wherein said displacing fluid is a gas.

4. A system according to claim 3, wherein said displacing fluid is a liquid.

5. A system according to claim 4, further comprising a collecting conduit (28) which during the first operating phase is connected to the first pumping means, and sample and buffer solution is passed from the first pumping means (10) to the valve means (30) and during the second operating phase is connected to the second pumping means and rinsing liquid is pumped into said conduit (28) by the second pumping means (12).

6. A system according to claim 2, further comprising
   (a) a sample connection (20,14) and a buffer solution connection (22,16) which are combined at the outlet side of the first pumping means (10) to form a collecting conduit (28) which communicates with a collecting conduit port (50) in the valve means (30),
   (b) a rinsing liquid connection (38,34) at the outlet side of the second pumping means (12) being connected by conduit (34) to the collecting conduit (28), and
   (c) the collecting conduit port (50) communicating, in the first valve position, with the first end of the ion exchanger column (72), and, in the second valve position, with a discharge port (70).

7. A system according to claim 1 wherein:
   (a) said analytical instrument is an atomic absorption spectrometer (78) with a furnace (88) for electrothermal atomization of the sample, and
   (b) said dosing capillary (64) is insertable into a sample inlet port (90) of the furnace (88) for introducing the sample.

8. A system according to claim 7, wherein the volume of the dosing capillary (64) is less than the accommodation capacity of the furnace (88).

9. A system according to claim 1, wherein said ion exchanger column (72) taper from the second end (76) to the first end (74).

10. A system according to claim 1, wherein said first and second pumping means (10,12) are formed by peristaltic pumps, respectively.

* * * * *

UNITED STATES PATENT AND TRADEMARK OFFICE
CERTIFICATE OF CORRECTION

PATENT NO. : 5,071,624
DATED : December 10, 1991
INVENTOR(S) : Michael Sperling

It is certified that error appears in the above-identified patent and that said Letters Patent is hereby corrected as shown below:

Column 1, line 53, after "in" insert --"Analytical Chemistry", 57 (1985), 21-25 and a publication"

Column 4, line 60, after "is" insert --connected to a --
Column 8, line 31, delete "4" and insert --2--
Column 8, line 63, delete "taper" and insert "tapers"

Signed and Sealed this

Fifteenth Day of June, 1993

Attest:

MICHAEL K. KIRK

Attesting Officer

Acting Commissioner of Patents and Trademarks